US005608150A

United States Patent [19]

Conner

[11] Patent Number: 5,608,150
[45] Date of Patent: Mar. 4, 1997

[54] FRUIT SPECIFIC PROMOTERS

[75] Inventor: Timothy W. Conner, Eureka, Mo.

[73] Assignee: Monsanto Company

[21] Appl. No.: 406,857

[22] PCT Filed: Jun. 27, 1994

[86] PCT No.: PCT/US94/07072

§ 371 Date: Mar. 20, 1995

§ 102(e) Date: Mar. 20, 1995

[87] PCT Pub. No.: WO95/02696

PCT Pub. Date: Jan. 26, 1995

[51] Int. Cl.⁶ .............................. A01H 1/00; C12N 5/04; C12N 15/29; C12N 15/82

[52] U.S. Cl. ........................... 800/205; 800/DIG. 44; 536/23.6; 536/24.1; 435/69.1; 435/70.1; 435/172.3; 435/194; 435/411; 435/419

[58] Field of Search ................... 536/23.2, 24.1, 536/23.6; 435/69.1, 70.1, 172.3, 240.4, 194; 800/205, DIG. 44

[56] References Cited

FOREIGN PATENT DOCUMENTS 0409629  1/1991  European Pat. Off. .
9119806 12/1991  WIPO .

OTHER PUBLICATIONS

Wingate et al. 1991. Plant Physiol. 97: 496–501.

*Primary Examiner*—David T. Fox
*Attorney, Agent, or Firm*—Grace L. Bonner; Dennis R. Hoerner, Jr.

[57] ABSTRACT

TFM7 and TFM9, promoters for expression of a gene of choice in fruits such as tomato; DNA molecules, plant cells and plants containing them.

13 Claims, No Drawings

FRUIT SPECIFIC PROMOTERS

BACKGROUND OF THE INVENTION

Recent advances in genetic engineering have provided the requisite tools to transform plants to contain foreign genes. It is now possible to produce plants which have unique characteristics of agronomic and crop processing importance. The ability to chose the tissues in which to express such foreign genes and the time during plant growth to obtain expression is possible through the choice of a regulatory sequence which turns on the gene, called the promoter. A wide range of promoters are known for various plants, plant tissues, and developmental stages.

The tomato is a very important plant for genetic engineering. It is readily transformed to express foreign genes and has many characteristics which are known to be improved by certain genes. It is also a valuable crop plant in many countries and was the first transgenic food crop approved for sale in the U.S.

Promoters useful in expressing foreign genes in tomato and other fruits are known. For example, the solids content of tomato fruit can be increased by expressing an ADPglucose pyrophosphorylase gene behind a fruit specific promoter. (Kishore, PCT Appl. WO 91/19806). The promoter from the 2A11 genomic clone (Pear, et al. (1989) *Plant Mol. Biol.* 13:639–651) will control expression of ADPglucose pyrophosphorylase in tomato fruit. The E4 and E8 promoters (Deikman, et al. (1988) *The EMBO Journal* 7:3315–3320), as well as the promoter for polygalacturonase are known to be fruit specific. However, the last three are limited to expression during a late stage in the development of the tomato fruit and so are known as red fruit promoters. The 2A11 promoter will cause expression during early stages, but is weaker than desired for some genes. Therefore, there is a need for stronger promoters which will cause expression of a gene during the development of the green fruit.

It is an object of the present invention to provide such promoters. It is a further object of the present invention to provide promoters which will function as fruit-specific in tomatoes and other fruit-bearing crops. It is a still further object of the present invention to provide DNA constructs containing these promoters and a gene encoding a desired protein or the antisense sequence for a less desirable protein.

SUMMARY OF THE INVENTION

The present invention provides two fruit-specific promoters which provide for expression at greater levels during early development of the fruit body of a plant. The two promoters are (1) TFM7 which is a DNA fragment of about 2.3 kb, of which 1.4 kb of the 3' end is shown in SEQ ID NO:1; and (2) TFM9 which is a DNA fragment of about 900 bp, of which bp of the 3' end is shown in SEQ ID NO:2.

The present invention also provides a recombinant, double-stranded DNA molecule comprising in sequence:
(a) a promoter selected from the group consisting of TFM7 and TFM9;
(b) a structural DNA sequence that causes the production of an RNA sequence which encodes a desired protein; and
(c) a 3' non-translated region which functions in plant cells to cause transcriptional termination and the addition of polyadenylated nucleotides to the 3' end of the RNA sequence, wherein said promoter is heterologous with respect to said structural DNA. Plant cells and whole plants containing this DNA construct are also provided.

Plants in which this DNA construct may be used include, but are not limited to, tomato, strawberry, and raspberry.

DETAILED DESCRIPTION OF THE INVENTION

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complimentary strand of RNA.

Novel fruit specific promoters exhibiting high and specific expression during the development of the tomato fruit have been isolated. A differential screening approach utilizing a tomato fruit cDNA library was used to identify suitable cDNA clones that expressed specifically in green fruit. cDNA probes, prepared from mRNA extracted from fruit at early and late developing stages and from combined leaf+stem tissue of tomato, were used. Clones that expressed abundantly in green fruit and that showed no detectable expression in leaves were identified. Genomic Southern analysis indicated a small (1–2) gene copy number. The promoters for these cDNA clones were then isolated by screening a tomato genomic clone bank. The expression pattern of these promoters is confirmed by fusion to the β-glucuronidase (GUS) gene and by following the expression of the GUS enzyme during development in transgenic fruit. Results are given below in Example 1.

These promoters have been fused to the CTP-glgC16 construct described in WO 91/19806. Results of transformation of tomatoes with the TFM7 construct are shown in Example 2. Alternatively, in order to increase sucrose content in fruit, one might want to inhibit the action of the plant ADPGPP gene by incorporating an antisense sequence corresponding to one or both of the subunits of ADPGPP. Use of the promoters of the present invention could be a convenient means to do this at the early fruit stage.

Other genes which might be usefully fused to a promoter of the present invention include sucrose phosphate synthase (SPS), which is thought to control the overall rate of sucrose biosynthesis in plant cells. Expression of an SPS gene, driven by TFM7 or TFM9, may result in a developing fruit with stronger sink activity.

Another possible use is with an invertase gene. Expression of invertase in a sink cell such as in a fruit is another method for increasing the ability of a cell to act as a stronger sink by breaking down sucrose to metabolites that can be used in carbon utilization pathways, e.g., starch biosynthesis. More sucrose is then mobilized into the sink tissue. Expression of invertase in the proper tissue and cellular compartments when the fruit is a strong sink, i.e., in a green fruit, is highly desirable.

Lastly, the use of the promoters of the present invention with a gene for sucrose synthase would be desirable for the reasons given for SPS.

Plant Transformation/Regeneration

A double-stranded DNA molecule containing one of the promoters of the present invention can be inserted into the genome of a plant by any suitable method. Suitable plant transformation vectors include those derived from a Ti plasmid of *Agrobacterium tumefaciens,* as well as those disclosed, e.g., by Herrera-Estrella, et al. (1983) *Nature* 303:209; Klee, H. J., et al. (1985) *Bio/Technology* 3:637–42; and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A particularly useful Agrobacterium-based plant transformation vector for use in transformation of dicotyledonous plants is plasmid vector pMON505 (Rogers, S. G. et al. (1987) "Improved Vectors for Plant Transformation: Expression Cassette Vectors and New Selectable Markers" in *Methods in Enzymoloay,* ed. Wu and Grossman, pp 253–277, San Diego: Academic Press). Binary vector pMON505 is a derivative of pMON200 in which the Ti plasmid homology region, LIH, has been replaced with a 3.8 kb HindIII to SmaI segment of the mini RK2 plasmid, pTJS75 (Schmidhauser, T. J. and D. R. Helinski. (1985) *J. Bacteriol.* 164–155). This segment contains the RK2 origin of replication, oriV, and the origin of transfer, oriT, for conjugation into Agrobacterium using the tri-parental mating procedure (Horsch, R. B. and H. Klee. (1986) *PNAS U.S.A.* 83:4428–32). Plasmid pMON505 retains all the important features of pMON200 including the synthetic multi-linker for insertion of desired DNA fragments, the chimeric NOS/NPTII/NOS gene for kanamycin resistance in plant cells, the spectinomycin/streptomycin resistance determinant for selection in *E. coli* and *A. tumefaciens,* an intact nopaline synthase gene for facile scoring of transformants and inheritance in progeny and a pBR322 origin of replication for ease in making large amounts of the vector in *E. coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON 17227. This vector is described by Barry et al. in WO 92/04449 and contains a gene encoding an enzyme conferring glyphosate resistance which is an excellent selection marker gene for many plants.

When adequate numbers of cells (or protoplasts) containing the gene of choice driven by a promoter of the present invention are obtained, the cells (or protoplasts) are regenerated into whole plants. Choice of methodology for the regeneration step is not critical, with suitable protocols being available for hosts from tomato and peppers.

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

EXAMPLE 1

Two of the green fruit promoters, described above and designated TFM7 and TFM9, were isolated and characterized from a *Lycopersicon esculentum* cv. VF36 genomic library. For each of these a partial sequence of the 5' terminus, untranslated and promoter regions from which the promoter was derived is herein provided. SEQ ID NO:1 is for TFM7. The 2.3 kb promoter fragment has as a 5' end the internal XbaI site and extends to the putative translation initiation point (modified by placing a BglII recognition site at this latter point). SEQ ID NO:2 is for TFM9. The ~900 bp TFM9 promoter fragment extends from the internal SalI site to the putative translation initiation point (modified by placing a BglII recognition site at this latter point).

Each of these promoters has been fused to the GUS gene and transformed into tomatoes. Regenerated tomato plants were observed for evidence of expression of GUS throughout their life cycle. The results are shown in Tables 1 and 2. All values given therein represent the mean with standard error from at least 3 fruit harvested from 3 or 4 R1 GUS positive plants from a transgenic line. GUS activity readings from several floridade wild-type control plants are also indicated. Developmental and tissue stages are Immature Green 1 (2–3 cm fruit), Immature Green 2 (4–5 cm fruit), Mature Green fruit (at least 2 locular cavities are filled), Turning (10–20% of the fruit is pink or red) and young leaf. "ND" means no detectable units recorded. In Table 1, transgenic lines 11541, 11420,and 11305 are selected lines containing the pTFM7/GUS/nos construct. In Table 2, transgenic lines 11256, 11269, and 11290 are selected lines containing the pTFM9/GUS/nos construct.

TABLE 1

|  | 11541 | 11420 | 11305 | Floridade |
|---|---|---|---|---|
| Imm Gm 1 | 58620 ± 3371 | 21670 ± 7555 | 6338 ± 773 | 12 |
| Imm Gm 2 | 71887 ± 5657 | 19933 ± 6401 | 5805 ± 900 | 14 |
| Mature Gm | 45243 ± 8666 | 14723 ± 12636 | 6334 ± 1358 | 26 |
| Turning | 34937 ± 6273 | 4780 ± 1470 | 5293 ± 901 | 39 |
| Leaf | 49 ± 70 | 19 ± 32 | 103 ± 61 | ND |

TABLE 2

|  | 11256 | 11269 | 11290 | Floridade |
|---|---|---|---|---|
| Imm Gm 1 | 36283 ± 4822 | 109682 ± 23956 | 20737 ± 535 | 12 |
| Imm Gm 2 | 31793 ± 7382 | 104445 ± 22885 | 13530 ± 1091 | 14 |
| Mature Gm | 14663 ± 1650 | 89115 ± 34585 | 5377 ± 1491 | 26 |
| Turning | 8468 ± 2171 | 33003 ± 5159 | 2309 ± 883 | 39 |
| Leaf | 210 ± 101 | 498 ± 166 | 83 ± 22 | ND |

EXAMPLE 2

TFM7 and TFM9 were fused to the chimeric CTP-GlgC16 gene (and suitable 3' sequences) disclosed in WO 91/19806, and the expression cassettes were moved into a plant transformation vector, as discussed below.

The TFM7 promoter was ligated into the vector pMON999 for ease of manipulation, resulting in the plasmid pMON16987. Fusion with the CTP-glgC16 chimeric gene was achieved through a triple ligation of the Hind III-Bgl II TFM7 promoter fragment from pMON16987, with a Bgl II-Sac I fragment from pMON20102 (contains the chimeric gene, disclosed in WO 91/19806), and placing this into the binary plant transformation vector pMON10098 (See FIG. 11 in WO 91/19806) digested with Hind III and Sac I. This plasmid, pMON16989, was subsequently used to transform tomato variety UC204C.

The TFM9 promoter was fused to CTPi-glgC16 essentially as described above. The SalI-BamHI TFM9 promoter fragment plus GUS was ligated into pEMBL18+ cut with the same enzymes to give pMON22701. The TFM9 promoter could then be removed as a Hind III-Bgl II fragment (from pMON22701) and ligated with the CTPl-glgC16 Bgl II-Sac I fragment from pMON20102 into Hind III-Sac I digested pMON10098, resulting in pMON22709. This plasmid was used to transform tomato variety UC204C.

Tomato plant cells were transformed utilizing Agrobacterium strains by the method as described in McCormick et al. (1986). In particular, cotyledons are obtained from 7-8 day old seedlings. The seeds are surface sterilized by the following procedure: 1) soak seeds in water for 15 minutes; 2) soak in 70% EtOH for 1 minute, then rinse with sterile water; 3) soak in 1 N NaOH for 20 minutes; 4) rinse 2 times in sterile water; 5) soak in 25% Chlorox with Tween 20 for 25 minutes; 6) rinse in sterile, deionized water 3 times. The seeds are germinated in phyta trays (Sigma) on Davis germination media, as described above, with the addition of 25 mg/L ascorbic acid. The seeds are incubated for 2-3 days at 28° C. in the dark, and then grown in the growth chamber at 25° C., 40% humidity under cool white lights with an intensity of 80 einsteins $m^{-2}s^{-1}$. The photoperiod is 16 hrs of light and 8 hrs of dark.

Seven to eight days after initiating germination, the cotyledons are explanted as described above. The cotyledons are pre-cultured on "feeder plates" composed of Calgene media, plus acetosyringone and 1 mM galacturonic acid, containing no antibiotics, using the conditions described above.

Cotyledons are then inoculated with a log phase solution of Agrobacterium containing the plasmids described above. The concentration of the Agrobacterium is approximately $5 \times 10^8$ cells/ml. The cotyledons are allowed to soak in the bacterial solution for eight minutes and are then blotted to remove excess solution on sterile Whatman filter disks and are subsequently replaced to the original feeder plate where they are allowed to co-culture for 2-3 days.

Cotyledons are transferred to selection plates containing Davis regeneration media with 2 mg/l zeatin riboside, 500 µg/ml carbenicillin, and 100 µg/ml kanamycin. After 2-3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds will continue to regenerate. Shoots develop within 3-4 months.

Once shoots develop, they are excised cleanly from callus tissue and are planted on rooting selection plates. These plates contain 0.5× MSO containing 50 µg/ml kanamycin and 500 µg/ml carbenicillin. These shoots form roots on the selection media within two weeks. If no shoots appear after 2 weeks, shoots are trimmed and replanted on the selection media. Shoot cultures are incubated in percivals at a temperature of 22° C. Shoots with roots are then potted when roots are about 2 cm in length. The plants are hardened off in a growth chamber at 21° C. with a photoperiod of 18 hours light and 6 hours dark for 2-3 weeks prior to transfer to a greenhouse. In the greenhouse, the plants are grown at a temperature of 26° C. during the day and 21° C. during the night. The photoperiod is 13 hours light and 11 hours dark and allowed to mature.

Fruit from plants transformed with pMON16989 (TFM7 promoter) have been obtained and tested. TFM7 causes high expression of glgC16 enzyme in the green fruit (>0.1% extracted protein), but glgC16 expression is very weak or undetectable in the ripe fruit. TFM7 results in starch in the ripe fruit in some lines, while controls always have an iodine score of '0', indicating no starch. Juice from these fruits is very viscous, and soluble solids are increased in many of the lines. Comparison data is shown in Table 3. Soluble solids and starch rating were measured in serum from hot break tomato juice. Starch was measured by adding one drop of an iodine solution to filtered serum, and measuring color intensity on a 0-4 scale where yellow=0 (no starch) to dark blue=4 (high starch).

TABLE 3

| LINE | % BRIX | IODINE STAIN |
|---|---|---|
| 16989-10712 | 5.7 | 0 |
| 16989-10714 | 6 | 2 |
| 16989-10223 | 5.6 | 4 |
| 16989-10381 | 6.7 | 4 |
| UC204C | 5.8 | 0 |
| UC204C | 6.3 | 0 |
| UC204C | 5.4 | 0 |
| UC204C | 5.4 | 0 |
| UC204C | 5.4 | 0 |
| UC204C | 6.7 | 0 |
| UC204C | 5.2 | 0 |
| UC204C | 6 | 0 |
| UC204C | 6 | 0 |

I claim:

1. The fruit-specific promoter TFM7.
2. The fruit-specific promoter TFM9.
3. A recombinant, double-stranded DNA molecule comprising in sequence:
   (a) a promoter selected from the group consisting of TFM7 and TFM9;
   (b) a structural DNA sequence that causes the production of an RNA sequence which encodes a desired protein; and
   (c) a 3' non-translated region which functions in plant cells to cause transcriptional termination and the addition of polyadenylated nucleotides to the 3' end of the RNA sequence,
   wherein said promoter is heterologous with respect to said structural DNA.
4. The DNA molecule of claim 3 wherein the DNA sequence encodes ADPglucose pyrophosphorylase.
5. The DNA molecule of claim 4 wherein said enzyme is glgC16.
6. A plant cell comprising a recombinant, double-stranded DNA molecule comprising in sequence:
   (a) a promoter selected from the group consisting of TFM7 and TFM9;
   (b) a structural DNA sequence that causes the production of an RNA sequence which encodes a desired protein; and
   (c) a 3' non-translated region which functions in plant cells to cause transcriptional termination and the addition of polyadenylated nucleotides to the 3' end of the RNA sequence
   wherein said promoter is heterologous with respect to the said structural DNA.
7. The plant cell of claim 6 wherein the DNA sequence encodes ADPglucose pyrophosphorylase.
8. The plant cell of claim 7 wherein said enzyme is glgC16.
9. The plant cell of claim 6 wherein the cell is from tomato.
10. A tomato plant consisting of plant cells of claim 9.
11. The tomato plant of claim 10 wherein the DNA sequence encodes ADPglucose pyrophosphorylase.
12. An isolated DNA molecule comprising SEQ ID NO:1.
13. An isolated DNA molecule comprising SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 1478 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO: 1:

```
AGCCTTGTGT  TAGGGGGTAT  TCAAACCTTC  TTTGACTGAA  AATTTTATTA  TTTATACATG        60
```

```
TTTAAAATTA CTTTTTAATC TATATATAAT AGATATCAAT CCTTCATTTA ATTGTATTTT      120

TGTATTAATT CTATAAATAT TAAATTACTT TATTAAAAAT TCTAATTCTG TCACTCGTCA      180

TTTCATAATA TTCTTGACGG TGATGGTAGT GATAATTACG TTGATTGGAG CCACATGGGC      240

CGCTACTTTT TAAAAGGATG AACCTTGGAA TGTAGTGAAT GTTGAGTCTC ATAGCTCACT      300

CACGGACTCA ACAGCAAAAT CTGTCCTCTT TTTCCCTTCT CCAATTCACA TACTGTCACT      360

TGGACAAATA ATATTTGAAA ATTTTGGCCT AAAGTTAGGT TTGGAGCCGT ATGGTAATTT      420

GATACACAAA TTATTATATA ATTGATATAT CAGGTATATA TATCAAGTTG TCGCTTCTTC      480

GTTCATTGTT TCTCTCACTA AAATTTTCAA TTCACTTTTT AAAAAATCGA TAAATTTTTA      540

ATATAACTTT ACATAACATA TTCAAAATTA CAAAATAAA GGATATTTTT ATATGTTTAT       600

TTTTAATGTA AGATTAAATA TTTAGAATTC TTTTTAAGAA CGGTACAAGC AAATTAAAAG      660

AGAGAAGGTA TATTAGTGGG CCTATGTATC TTTGATATCA TATGCCTCTC AAAGAGCATC      720

CTGATGAGTC TATATATCTT TGTTGATAGT GATTAACCA TTTATGTATG TACGTAGTAC       780

TAAGACATGT TAAATAAGAT CCTAGAGAAA GATTTTTGGA AAAGTGAAAA CAGCAATAAA      840

GAAAAGTCAT TTAAACACTT TCCAACAAAC ATTTGGTAAT CGATTTTAAT TACCCACTTA      900

AACAAAACTA TTTGTACGTA AAATGTTTAA GTAGAAAAGA GATTTTTTA  AAAAAAAAAA      960

GAAGGCAAGA GGTCATATAT CTGACCCTTC CTTAAATCCC CGCGTATAAC ACTTTCTTTT     1020

TTTTGTGTGT GTATGTTCAG GAACATTTGT ATTTCTATT  TGAAATTTCT CATTAAGTCA     1080

AATTCGAAAT CTTTTAAATA ATGTAGAGAA ATCTCATTAT ATTTAACAAT CCCACTTGAT     1140

GAATTCCTAA ACATTTTCTA TAAAATAACA CTAAATCTTT AATTATACAT ATTACATACC     1200

TAACTCAAGC AATCTTGTCG GAAAATCAT  TAGAAAAGAA TTGGAAATAG GGAAATAAAT     1260

AGACATATTT TGGTTAGTAT CTTTGTCTAT AAGAATGGGT GTGTTAAAGA GCTAGTGCCA     1320

TAGTGTACCA TTCTATTGGT AGCATTTGGC AAGAGTTATT CCCTCTCTCC ATACCAATGG     1380

AGAAGTTTAA TCTTGCTAGA GTCTTATTGT TGCTTCTTCA ACTTGGAACT TTGTTCATTG     1440

CCCATGCATG TCCTTATTGT CCATATCCTC CTTCCACC                            1478
```

( 2 ) INFORMATION FOR SEQ ID NO: 2:

( i ) SEQUENCE CHARACTERISTICS:
        ( A ) LENGTH: 450 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 2:

```
AAATAAATAT TTCAAAGTAA ATTGTTACTC CCTCTATCCC ATACTCTTTT CTTTTTTTAA       60

TCGATTTCTT ACTCTAATTG AACTATTGGA GACAACTTAA ATGTAAATTT TTTTTTTCTT      120

TATCAAAATG ATTGGCTGCT ATATAAATAT CTAATGGTTA TTATACATAA ATTTTAATAT      180

TTTTTATAAA AAAATATCGA GCTAAATCAT ATCGTTTAAA TATAGAGATG TGTTATTTAT      240

TTAAAAATTA ATTTTAAAAA AGTGAATATT GTAAATTAGG ATGAAAGAGT ATTATATTGG      300

TTGTCGCAGT ATAAATACCC TGCATGCCAT TACATTTGTT CAATCATCTT TGCAACGATT      360

TGTGTGCTTT AGCTTCCTTA CATAACATGG CTTCTATAAC TAAAGCCTCA TTACTTATCC      420

TTTTCCTCTC CTTGAATCTC CTTTTCTTCG                                      450
```